United States Patent [19]

Essex et al.

[11] Patent Number: 5,068,174
[45] Date of Patent: Nov. 26, 1991

[54] T-CELL LYMPHOTROPHIC VIRUS PROTEIN AND ASSAY

[75] Inventors: Myron E. Essex, Sharon; Jonathan S. Allan, Westwood; Tun-Hou Lee, Newton, all of Mass.

[73] Assignee: President and Fellows of Harvard College, Cambridge, Mass.

[21] Appl. No.: 250,309

[22] Filed: Oct. 25, 1988

Related U.S. Application Data

[62] Division of Ser. No. 795,997, Nov. 7, 1985.

[51] Int. Cl.[5] .......................................... G01N 33/569
[52] U.S. Cl. ...................................... 435/5; 435/7.92; 435/7.93; 435/7.94; 435/7.95; 435/974; 435/975; 530/350; 530/395
[58] Field of Search ..................... 435/5, 7, 7.92-7.95, 435/974, 975; 530/350, 395

[56] References Cited

U.S. PATENT DOCUMENTS 4,520,113  5/1985  Gallo et al. .
4,554,101  11/1985  Hopp .

FOREIGN PATENT DOCUMENTS 0187041  9/1986  European Pat. Off. .

OTHER PUBLICATIONS

Hahn, "Molecular Cloning and Characterization of the HTLV-III Virus Associated with AIDS", Nature 312 (1984) 166-9.
Ratner et al, "Complete Nucleotide Sequence of the AIDS Virus, HTLV-III", Nature, 313 (1/1985) 277-84.
Hattori et al., "Identification of gag and env Gene Products of Human T-Cell Leukemia Virus (HTLV)", Virology 136(1984) 338-47.
Sanchez-Pescador et al., "Nucleotide Sequence and Expression of an AIDS-Associated Retrovirus (ARV-2)", Science 277 (2/1985) 484-92.
Schupbach et al., "Serological Analysis of a Subgroup of Human T-Lymphotropic Tetroviruses (HTLV-III) Associated with AIDS", Science 224 (1984) 503-5.
Watanabe et al., "HTLV Type I (U.S. Isolate) and ATLV (Japanese Isolube) Are the Same Species of Human Retrovirus", Virology, 133 (1984) 238-41.
Starcich et al., "Characterization of Long Terminal Repeat Sequences of HTLV-III", Science 227 (1985) 538-40.
Gallo et al., "The Family of Human T-Cell Leukemia Viruses and Their Role in the Cause of T-Cell Leukemia and AIDS", Dev. Biol., 28(RNA Tumor Viruses, Oncog. Hum. Cancer, AIDS), 1985: 191-205.
Crowl et al., HTLV-III env Gene Products Synthesized in E. coli are Recognized by Antibodies Present in the Sera of AIDS Patients; Cell, 41: 979-86; Jul. 1985.
Wain-Hobson et al.; Nucleotide Sequence of the AIDS Virus, LAV; Cell; 40:9-17; Jan. 1985.
Allan et al.; A New HTLV-III/LAV Encoded Antigen Detected by Antibodies from AIDS Patients; Science; 230: 810-13; Nov. 1985.
Lee et al.; A New HTLV-III/LAV Protein Encoded by a Gene Found in Cytopathic Retroviruses; Chemical Abstracts 104:137; 1986.
Markham et al.; Etiology of AIDS: Biological and Biochemical Characteristics of HTLV-III; Chemical Abstracts, vol. 104; 1986.
Proc. Nat'l. Acad. Sci. 82 (1985) 7748-7752.
Nature, 313 (1985) 450-458.
Nature, 312 (1984) 166-169, Hahn et al.
Science, 226 (1984) 57-61, Lee et al.
Science, 226 (1984) 61-65, Slamon et al.
(List continued on next page.)

Primary Examiner—Christine Nucker

[57] ABSTRACT

Cells infected with HTLV-III yield a protein (p27) having an apparent molecular weight of about 27,000 daltons. The presence in a biological specimen of p27 antigenic dterminants, or of antibodies to p27 antigenic determinants is useful information (by itself or as a panel of tests) for predicting the course of HTLV-III infection in seropositive patients. Polypeptides and antibodies used to perform assays to provide that information are disclosed, as well as assays and kits for such assays.

8 Claims, 3 Drawing Sheets

OTHER PUBLICATIONS

Science, 225 (1984) 419-121, Haseltine et al.
Science, 225 (1984) 381-385, Sodroski et al.
Nature, 312 (1984) 760-763.
Schüpbach et al., Science, vol. 224, pp. 503-505 (1984).
Potocnjak et al., Science, vol. 215, pp. 1637-1639 (1982).
Sarngadharan et al., Science, vol. 224, p. 506 (1984).
Kitchen et al., Nature (London), vol. 312, p. 367 (1984).
Robey et al., Science, vol. 228, p. 593 (1985).
Barin et al., Science, vol. 228, p. 1094(1985).
Allan et al., Science, vol. 228, p. 1091 (1985).
Sarngadharan et al., PNAS USA, vol. 82, p. 3491 (1985).
Virology 136, 338-347 (1984) Hattori, et al.
Chem. Abstr., vol. 104, (1986) 312905.
Chem. Abstr., vol. 104 (1986) 162-752.
Proc. Natl. Acad. Sci., vol. 82, pp. 8359-8363 (1985) Kiyokawa, et al.
Proc. Natl. Acad. Sci., vol. 78 (1981) pp. 3824-38-38, Hopp, et al.
Science, vol. 228, (1985) 93-96.
Nature, vol. 313, (1985) 277-284, Ratner, et al.
Nature, vol. 315, (1985) 151-154.
Cell, vol. 41, 979-986 (1985).
Chem. Abstr., vol. 104, (1986) 182972.
Chem. Abstr.: vol. 103 (1985) 52370.
Chem. Abstr., vol. 104, (1986) 1644.
Proc. Natl. Acad. Sci., vol. 81, 6202-6206 (1984) Kiyokawa, et al.
Chem. Abstr., vol. 102, (1985) 42-43.

T-CELL LYMPHOTROPHIC VIRUS PROTEIN AND ASSAY

This invention was made in the course of work for the NIH under grants CA37466, CA23885, and CA2T32-CA09031, and the United States Government has certain rights in the invention.

This is a divisional of co-pending application Ser. No. 795,997 filed on 11/7/85.

BACKGROUND OF THE INVENTION

This invention relates to novel purified forms of a protein found in cells infected with human T-cell lymphotrophic virus III (HTLV-III) and related viruses; the invention also relates to polypeptides, kits, and assays for detecting in a biological specimen the presence of that protein's antigenic determinants or of antibodies to one or more such antigenic determinants. For convenience, the term "HTLV-III related viruses" is used in this application to include viruses that are closely related to HTLV-III by serological biochemical and molecular criteria, including lymphadenopathy associated virus (LAV) (see Barre-Sinoussi (1983) Science 220:859), ARV (see Sanchez-Pescador (1985) Science 227:484) and AAV, and other forms, subtypes and variants, including simian viruses. The terms "human T-cell lymphotrophic virus" and "human T-cell leukemia virus" are used interchangeably, although the former is preferable.

Human T-cell lymphotrophic virus III (HTLV-III) is believed to play a key role in the pathogenesis of acquired immunodeficiency syndrome (AIDS). It has been shown that human patients whose bodies contain antibodies to HTLV-III-infected cells are apparently latently or actively infected with the virus. There are various tests to determine the presence of antibodies to HTLV-III proteins in a biological specimen. For example, an ELISA test is widely used for blood bank screening. For such assays, the goal is to screen out all individuals who have been exposed to HTLV-III, whether or not such individuals have developed or will develop AIDS.

Other HTLV-III-encoded polypeptides that are antigenic when expressed in infected individuals include:

1) a 55 kd gag polyprotein (p55) which yields a 24 kd protein (p24) as the major virus core protein and a 17 kd phosphoprotein (pp17) (Schupbach et al. (1984) Science 224:503-505); and 2) a gp160 env polyprotein which gives rise to gp120 at the amino terminus (see Essex and Lee, U.S. Ser. No. 670,361, filed Nov. 9, 1984, which is hereby incorporated by reference).

The disease course for patients who exhibit HTLV-III antibodies varies; some such patients are healthy and currently uninfected, others harbor the virus with few symptoms, still others have chronic symptoms that have been designated "AIDS related complex" (ARC), and, finally, some such individuals are AIDS patients, exhibiting immunodeficiencies that are ultimately fatal. It also appears that some ARC or non-symptomatic patients harboring the virus may develop AIDS after prolonged periods.

SUMMARY OF THE INVENTION

Cells infected with HTLV-III and related viruses yield a protein coded by the open reading frame (ORF) positioned 3' to the env gene. The protein coded by HTLV-III has an apparent molecular weight of about 27,000 daltons, meaning that, when myristylated, the protein migrates in conventional sodium dodecyl sulfate (SDS) electrophoresis gels as described below in a manner that is characteristic of a molecular weight of about 27,000 daltons, even though the actual molecular weight may differ somewhat from 27 kd; when computed from the viral coding sequence, the HTLV-III protein's molecular weight may be lower, e.g., about 22,000 daltons. For convenience, we refer to the protein coded by the open reading frame 3' to the env gene of HTLV-III and HTLV-III related viruses as "p27". The presence of p27, p27 antigenic determinants, or antibodies to p27 antigenic determinants in patients that are positive for HTLV-III or related viruses is useful information (by itself or as part of a panel of tests) for predicting the course of the infection in that patient.

Accordingly, in a first aspect, the invention features substantially pure polypeptides that are useful for assaying for HTLV-III and related viruses antibodies in a human biological specimen. The substantially pure polypeptides contain at least one antigenic determinant that is immunologically cross-reactive with the determinants of a p27 protein obtained from infected cells. By "polypeptides containing immunologically cross-reactive antigenic determinants" is meant polypeptides having in common antigenic determinants with which a given antibody will react.

Polypeptides according to the first aspect include the p27 protein itself either myristylated or unmyristylated. If myristylated at the NH, terminal, the polypeptide is blocked against Edman degradation. The polypeptides can also include myristylated or unmyristylated fragments of p27. Other useful polypeptides which have the necessary immunogenic determinants include peptides coded by HTLV-III and related viruses as well as synthetic polypeptides, e.g. produced by genetically engineered cells. Preferably, the polypeptide is labeled for use in an assay as described below.

Polypeptides according to the first aspect also include antibodies or fragments thereof which are anti-idiotypic towards the active determinant or determinants on the p27 protein of the invention. It has been shown that anti-idiotypic reagents are useful as diagnostic tools for the detection of antigens carrying sites which are immunologically cross-reactive with those on the antibodies (Potocnjak et al., Science 215:1637-1639 (1982)). Thus, an assay for p27 antibodies could be carried out with the aid of an anti-idiotypic antibody or immunologically active fragment thereof which carries an antigenic site or sites thereon which are immunologically similar to the antigenic site or sites on p27. Such anti-idiotypic antibodies can be raised against primary antibodies having specificity against the antigenic sites on the p27 of the invention (i.e. the anti-idiotypic antibodies are anti-antibodies). Preferably monoclonal anti-idiotypic antibodies are used.

As noted above, the presence of p27 antibodies provides useful information concerning the course of disease in individuals that are positive HTLV-III and related viruses. Accordingly, in a second aspect, the invention features a method of assaying a biological specimen for the presence of p27 antibodies, by incubating the specimen with the above-described polypeptide and determining whether or not an immunocomplex is formed.

In preferred embodiments of the second aspect, the assay for p27 antibodies is performed as part of a panel of tests for HTLV-III and related virus antibodies; thus, one or more specimens from the same patient is assayed for antibodies to other HTLV-III and related virus proteins such as one or more of the following proteins using techniques described in the above-cited references: p55, p24, p17, gp160, gp120, and gp41. The resulting information from positive patients provides an improved basis for estimating the course of the disease. For example, individuals exhibiting either p27 antibodies or p55/p24 antibodies are less likely to have contracted AIDS or ARC than individuals who are negative for both p55 and p24 antibodies; and those who are positive for both antibodies are even less likely to have contracted AIDS or ARC.

The invention also features assaying for the presence of a p27 antigenic determinant or for determinants cross-reactive with the determinants of p27. The determinants to be assayed may occur on p27 itself or on other polypeptides. The determinants may be in free circulation in body fluids or in lymphocytes. The assay can be carried out by known immunoassay methods, using antibodies, monoclonal or polyvalent, having immune reactivity with the antigenic determinants found on p27. For example competitive immunoassays or immunometric (sandwich) assays can be used.

Finally, the invention features antibodies that are useful in the above-described assays because they have antigenic determinants which are immunologically reactive with p27.

Other features and advantages of the invention will be apparent from the following description of the preferred embodiment and from the claims.

DESCRIPTION OF THE PREFERRED EMBODIMENT

Drawings

The Protein

The protein of the present invention, when myristylated, has a molecular weight of approximately 27,000 daltons as determined by sodium dodecyl sulfate (SDS) gel electrophoresis and is soluble in SDS buffer consisting of 0.15M sodium chloride, 0.05M Tris hydrochloride pH.7.2, 1% Triton X-100, 1% sodium deoxycholate, 0.1% sodium dodecylsulfate, and 1 mM phenylmethylsulfonyl fluoride. Triton X-100 is a nonionic detergent (octylphenoxy polyethoxy (9-10) ethanol). The p27 protein undergoes post-translational myristylation, and is not glycosylated. The unmyristylated moiety of the protein contains substantially the same antigenic determinant or determinants as does the myristylated protein. An $NH_2$-terminal myristylate group blocks Edman degradation.

Further characterization of the p27 protein, and indication that it is distinct from other, previously described HTLV-III specific proteins listed above, can be obtained by mapping the protein to HTLV-III DNA. p27 protein is obtained as described below from HTLV-III infected cells labeled with [$^3$H] leucine and [$^3$H] valine. The protein is fragmented with cyanogen bromide, and the fragments are separated by Sephacyl S-200 chromatography. Fractions are analyzed by Edman degradation and pooled.

Figure 1:
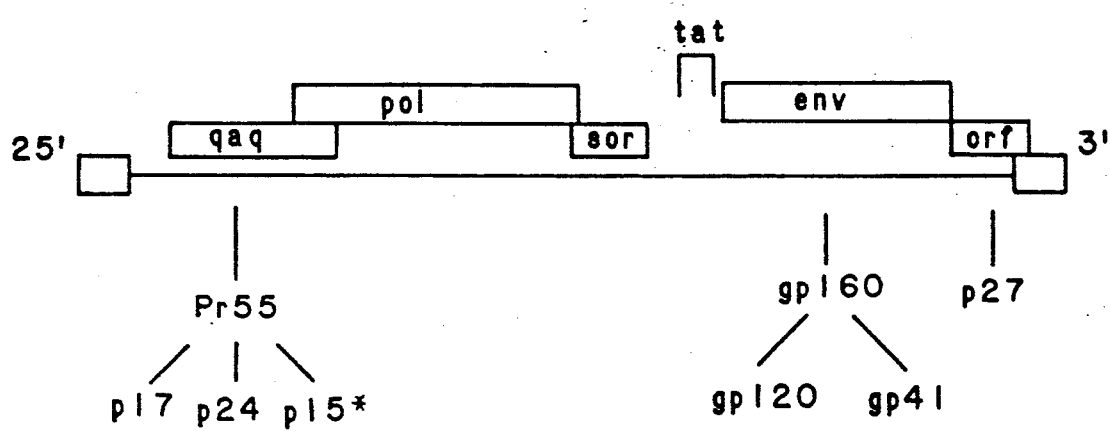
FIG. 1 is a diagrammatic representation of HTLV-III DNA indicating coding regions of various proteins.
Figure 2:
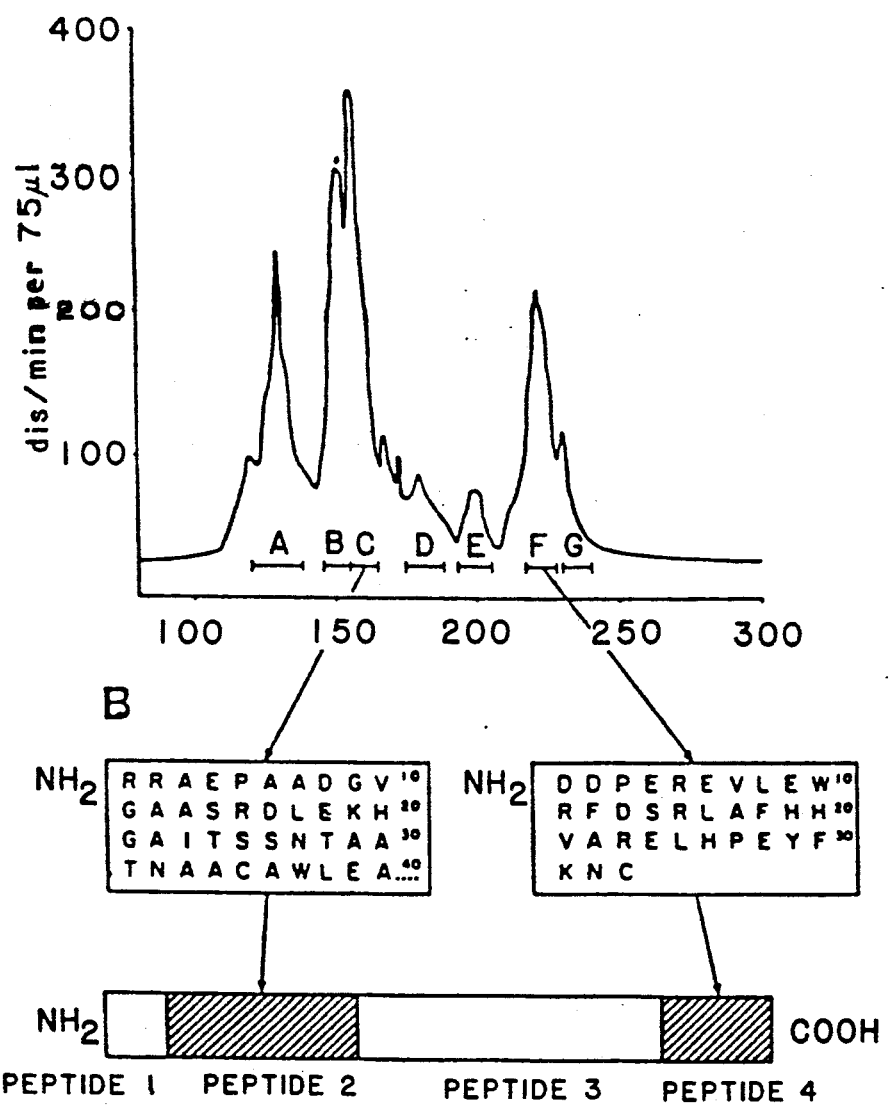
FIG. 2 is a graph depicting radioactivity detected in peptide fragments of p27 and depicting the am terminal amino acid sequence of two such peptide fragments.

FIG. 2 shows a diagrammatic representation of four peptides that are predicted to be generated by cyanogen bromide cleavage at met residues at positions 1, 20, 60, and 170 of the 204 amino acid sequence deduced from the 3' ORF of HTLV-III DNA. To match p27 to that HTLV-III DNA coding region, H9/HTLV-III$_{E-84-4}$ cells (described below) are metabolically labeled with 10 mCi of [$^3$H] leucine or [$^3$H] valine for four hours and cell lysates prepared. Radiolabeled lysates are precipitated with standard HTLV-III reference serum (same as FIG. 1, lane 2) and electrophoresed on 10% SDS-polyacrylamide gels. The p27 is excised from the gel, electroeluted and lyophilized prior to cyanogen bromide cleavage. Cyanogen bromide hydrolysis of p27 is accomplished by incubating the Protein for nine hours with two percent CNBr in seventy percent formic acid. The reaction is terminated with the addition of nine volumes of water and the mixture is lyophilized. Sephacryl S-200 separation of CNBr peptides and automated sequence analysis are performed by the general technique of Lee et al., Science (1984) 226:57 et seq. and Coligan et al. Methods Enzymol. (1983) 91:413. Fractions are collected, assayed for radioactivity, pooled, and subjected to Edman degradation. The sequences derived from pools C and F are compared to the amino acid sequences of CNBr cleavage products of the gene product coded by the 3' open reading frame (ORF) of HTLV-III derived from the DNA sequence data given by Meusing et al. (1985) Nature (London) 313:459 or Sanchez-Pescador (1985) Science 227:484.

The amino terminal sequence data derived from Edman degradation of peptides actually derived from pools C and F matches the predicted sequences shown in FIG. 2. Accordingly, the coding region for p27 is the open reading-frame (ORF) at the 3' terminal region of HTLV-III. The labeled amino acids are indicated by asterisks. It is likely that the methionine initiator sequence for the p27 coding region is the AUG codon in the 3' ORF which begins 5 nucleotides from the 3' end of the env gene and is followed by a glycine codon.

Figure 3:
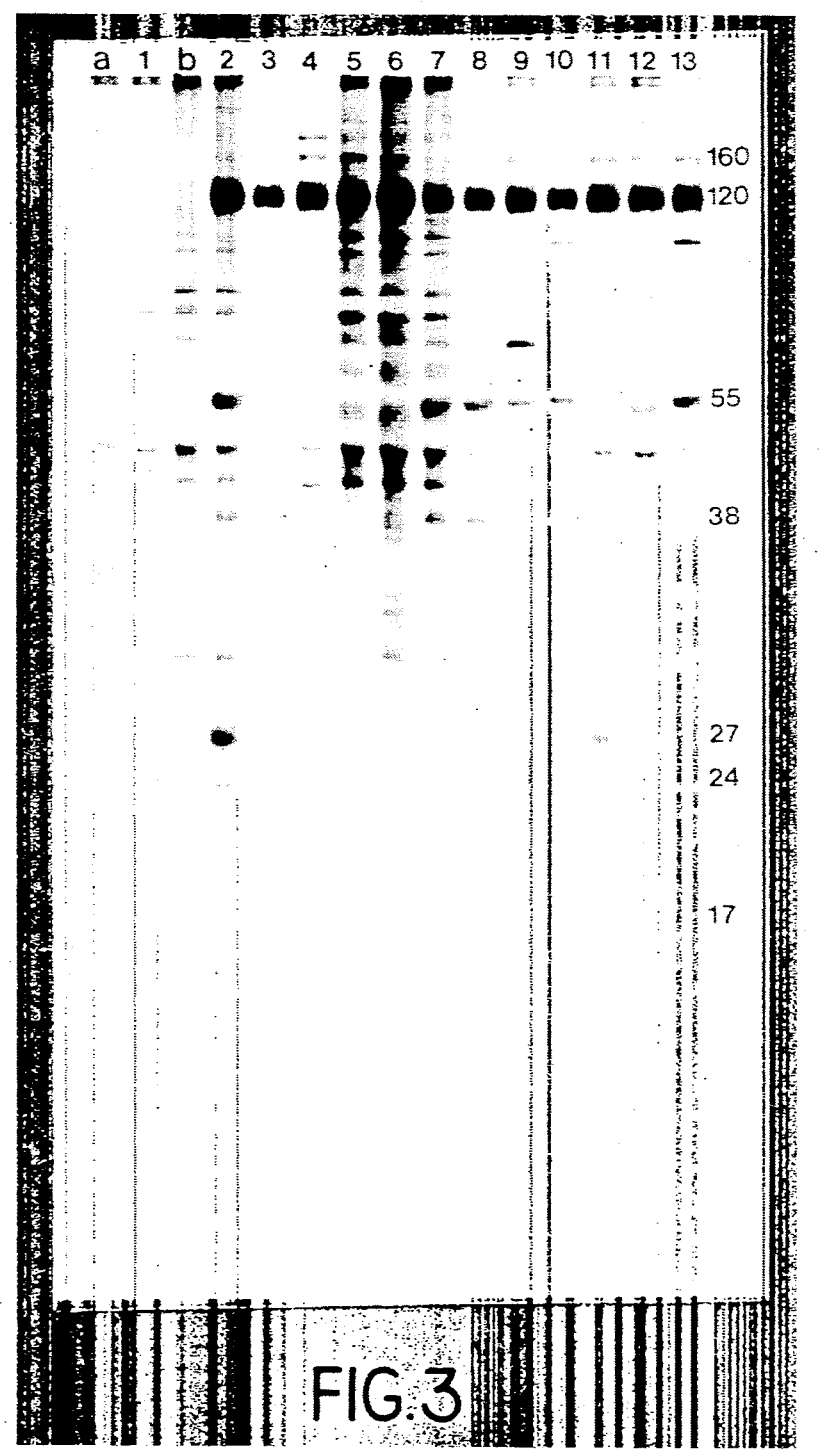
FIG. 3 is a photograph of SDS-polyacrylamide gels of radioimmunoprecipitates of HTLV-III infected cell proteins.

FIG. 3 is a photograph of an SDS-Page radioimmunoprecipitation of HTLV-III proteins showing antibody reactivities specific to p27. Cell lysates are prepared from [$^{35}$S] cysteine labeled H9/HTLV-III$_{E-84-4}$ cells or H9 uninfected cells. Radioimmunoprecipitation and SDS-PAGE are carried out by the method generally described in Kitchen et al. (1984) Nature 312:367; Barin et al. (1985) Science 228:1094; and Allan et al. (1985) Science 228:1091. Lysates are immunoprecipitated with the following sera: normal human serum pre-tested on uninfected H9 cells (lane a) and H9/HTLV-III$_{E-84-4}$ cells (lane 1); positive reference serum from an ARC patient pre-tested on uninfected (lane b) and infected cells (lane 2); serum from seven ARC patients (lanes 3, 4, 5, 8, 9, 10, and 13); serum from three AIDS patients (lanes 6, 11, and 12); and serum from one healthy homosexual male (lane 7). The serum of lanes 3-12 is tested on infected H9/HTLV-III$_{E-84-4}$ cells. Immunoprecipitates are electrophoresed on 20 centimeter 10% SDS-polyacrylamide gels.

OBTAINING THE PROTEIN

The protein can be obtained from HTLV-infected cells. A variety of cell lines have been prepared, which are permanently and persistently infected with HTLV; among them can be mentioned HTLV-III-infected H9 cells, Lymphadenopathy associated virus (LAV)-infected NC37 cells, and Molt 3 and HUT78 cells infected with fresh AIDS virus isolates. One particular such HTLV-III infected cell line is H9G/HTLV-III$_E$-84-4 (ATCC 8983), an isolate produced by repeated passage of H9/HTLV-III (ATCC 8543). It may be that the exact sizes of the novel protein is slightly different in different lines; however, the common immunologically cross-reactive portion of the protein is the same regardless of cell line, since it is a protein induced by HTLV. Thus, any cell which harbors the virus may be an appropriate source for the novel proteins.

In order to obtain the protein from any infected cells carrying the virus, the cells are metabolically labeled (e.g. with $^{35}$S-cysteine) and immunoprecipitated with antisera obtained from HTLV-III-infected subjects. The novel proteins can then be detected and isolated in the cell lysate by SDS gel electrophoresis.

A specific protocol of p27 preparation is as follows. Infected HTLV-III cells are harvested at their log phase of growth. After one wash with RPMI-1640 medium, each sample of the cells is resuspended in a labeling medium consisting of RPMI-1640 medium, 10% fetal bovine serum, and 100 $\mu$Ci/ml of $^{35}$S-methionine. At the end of about 4 to 8 hours pulsing, the radioactive labeled cells are washed three times with cold PBS. The cell pellet is then lysed with 0.2 ml/1$\times$10$^6$ cells of cold lysis buffer (RIPA) (0.15M sodium chloride, 0.05M Tris-hydrochloride pH 7.2, 1% Triton X-100 wetting agent, 1% sodium deoxycholate, 0.1% sodium dodecyl sulfate, and 1 mM phenylmethylsulfonyl fluoride). After 10 minutes of intermittent vortexing, the mix is centrifuged for 1 hour at 100,000$\times$g at 4° C. and absorbed on Sepharose Cl-4B-protein-A beads. The lysate is then subjected to immunoprecipitation with positive anti-sera, and the immunoprecipitate is electrophoresed.

An alternative method for preparing the protein, the 3' ORF HTLV-III region can be isolated and cloned for expression in a bacterial expression system such generally using the technique described in Chang et al. (1985) Nature 315:151.

ASSAYS

The purified and isolated proteins or any polypeptide antigen immunologically cross-reactive therewith can be employed as a standard antigen in any conventional assay procedure for detection in biological specimens of the presence of antibodies specific thereto.

The proteins or polypeptides immunologically cross-reactive therewith can be labeled by conventional procedures with $^{125}$I or $^{35}$S or $^3$H for use in radioimmunoassay, with fluorescein for flourescent immunoassay, with enzyme for enzyme immunoassay or with biotin, for biotin-avidin linked assays. It can be employed, labeled or unlabeled as desired, in competitive immunoassays, as well as in double antibody assays using two antibodies, either of the idiotype:anti-idiotype variety or more particularly of the second antibody type using an anti-Fc antibody, or other assays.

To form the protein antibody complex, aliquots of protein-A-coated beads are bound to: (a) positive reference blood serum from an individual known to harbor antibodies against HTLV-III viral proteins; (b) negative control serum from individuals free from infection; and (c) serum from unknown individuals to be tested. Each aliquot of coated beads is then reacted with an aliquot of each precleared lysate obtained from cells according to the methods described above at 4° C. for 4–8 hours to permit complex formation or immunoprecipitation to occur between the bonded lysate protein and any antibody present in the sera. At the end of the reaction the beads are washed 5 times with the buffer (RIPA) to remove uncomplexed lysate protein.

The beads are then immersed in a sample buffer (0.1M Cleland's reagent, 2% sodium dodecylsulfate, 0.08M Tris-hydrochloride pH 6.8, 10% glycerol, and 0.2% Bromphenol Blue) and subjected to boiling at 100° C. for 2 minutes to elute proteins from the beads and to dissociate complexes.

Alternatively, the novel proteins or polypeptides immunologically cross-reactive therewith could be immobilized on an insoluble phase, such as an insoluble resin, and detection of the anti-protein antibodies can be carried out by measuring their binding to the insoluble phase. Insoluble phases also include latex particles, which when coated with the novel protein or its immunologically cross-reactive polypeptides and subjected to anti-protein antibody, will agglutinate. Yet other insoluble phases include test tubes, vials, titration wells, and the like, to which the novel protein or its immunologically cross-reative polypeptide can be bound, and antibody thereto detected by double antibody techniques or Protein-A dependent techniques.

The assay for p27 antibody may utilize the p27 protein in crude form and is not limited to using this protein in substantially pure form. For example, the protein may be substantially purified, or cruder mixtures can be used.

Preferably, the assay for p27 or p27 antibodies is performed on individuals who are seropositive, that is, who demonstrate the presence of antibodies to one of the relatively strongly antigenic glycoproteins (gp120, gp160, and gp41). The p27 antibody assay provides the following information:

| | Disease Course for HTLV-III (gp120) Seropositive Individuals | | | |
|---|---|---|---|---|
| | Symptom-free | ARC | AIDS | Total |
| anti-p27+ | 48.1% | 42.9% | 29.0% | 37.0 |

Also, preferably, knowledge that an HTLV-III positive patient has anti-p27 antibodies is combined with information gained from other tests to increase the reliability of an assessment of the course of the virus in that patient. For example, the presence of antibodies to other weakly antigenic HTLV-III or related virus proteins (e.g., p55 or p24) is further information to be used with the presence of anti-p27 antibodies. Such tests can be used as a panel to predict the disease course.

Preferably, the tests for the various HTLV-III antibodies are performed by the methods indicated in the following table:

| Antigen | Genomic Origin in Virus | Richest Source* | Optimal Procedures for Antibody Testing* |
|---|---|---|---|
| p55 | gag (entire) | IC* | WBIC, IPIC, CIF* |
| p24 | gag (middle) | CV | E, WBCV, WBIC, ICV, IPIC, CIF |

| Antigen | Genomic Origin in Virus | Richest Source* | Optimal Procedures for Antibody Testing* |
|---|---|---|---|
| p27 | 3' orf (entire) | IC | IPIC |

*Abbreviations: CIF, cytoplasmic immunofluorescence; CV, concentrated virus; E, ELISA; IC, infected cell; ICV, immunoprecipitation with concentrated virus; IPIC, immunoprecipitation with infected cell homogenate; WBIC, Western Blotting with infected cell homogenate; WBCV, Western blotting with concrated virus.

The elements necessary for carrying out the diagnostic methodology described hereinbefore may be present in a kit. Such kit comprises a carrier being compartmentalized to receive therein one or more containers, each of said containers comprising one or more elements necessary to carry out the tests.

For example, the first container may contain one or both of the purified protein p27 or its immunologically cross-reactive polypeptides in detectably labeled or in insolubilized form.

A second container may comprise anti IgG antibody, polyclonal or monoclonal, useful in double antibody binding assay, or elements needed for detection of the label on the protein or its immunologically cross-reactive polypeptides (e.g. chromogenic substrates).

Additional containers may comprise varying amounts of the protein or its immunologically cross-reactive polypeptides which can be used to prepare a standard curve into which experimental results can be interpolated. The materials may be present in the kit by themselves, in solution, freeze-dried, or in admixture with other inert materials, such as inert proteins, and the like.

The biological specimens tested may include blood, serum, lymphocytes, urine, tissues, saliva, feces, and the like. Other protein antibodies may be added to the test panel, for example, antibodies to proteins coded by viruses that are closely related to HTLV-III.

We claim:

1. A method of assaying a biological specimen for the presence of HIV antibodies indicative of HIV infection, comprising the steps of:
    (a) incubating a biological specimen in which the presence of HIV antibodies is to be detected with a composition comprising a marker consisting essentially of i) p27 (a protein encoded by the open reading frame 3' to the env gene of HIV), or ii) a fragment of p27 having an antigenic determinant that reacts with anti-p27 antibody, said incubating being for a sufficient time and under conditions to allow said p27 polypeptide or fragment to form an immunocomplex with antibody present in said specimen; and
    (b) then determining whether an immunocomplex is formed between said marker and antibody in said specimen, the formation of an immunocomplex being indicative of the presence of HIV infection.

2. The method of claim 1, wherein said marker is labeled.

3. The method of claim 1, further comprising the step of reacting said specimen with an HIV polypeptide lacking any antigenic determinant cross-reactive with said p27, for a sufficient time and under conditions to allow said HIV polypeptide to form an immunocomplex with antibody present in said specimen, and then determining whether an immunocomplex is formed between said HIV polypeptide and antibody in said specimen, the formation of an immunocomplex being indicative of the presence of HIV antibodies, other than p27-reactive antibodies, in the specimen.

4. The method of claim 3, wherein said HIV polypeptide is a gag or env polypeptide.

5. The method of claim 4, wherein said HIV polypeptide is p55, p24, gp41, gp160, gp120 or pp17.

6. The method of claim 1 wherein said marker is substantially pure p27 or a substantially pure fragment thereof.

7. A method of detecting the presence of a p27 antigenic determinant in a biological specimen, comprising the steps of:
    (a) incubating said biological specimen with antibody having specificity against said antigenic determinant for a sufficient time and under conditions allowing the formation of an immunocomplex between said antibody and antigen in said specimen, and then determining whether an immunocomplex is formed, the formation of an immunocomplex being indicative of the presence of a p27 antigenic determinant in said specimen.

8. A kit for detecting HIV antibody comprising a container containing:
    a composition comprising marker consisting essentially of: i) p27 polypeptide (a protein encoded by the open reading frame 3' to the env gene of HIV), or ii) a fragment of p27 having an antigenic determinant that reacts with anti-p27 antibody; and
    means for determining formation of an immunocomplex between said marker and anti-p27 antibody.

* * * * *

UNITED STATES PATENT AND TRADEMARK OFFICE
CERTIFICATE OF CORRECTION

PATENT NO. : 5,068,174
DATED : November 26, 1991
INVENTOR(S) : Myron E. Essex et al It is certified that error appears in the above-indentified patent and that said Letters Patent is hereby corrected as shown below:

In the abstract, line 5, "dterminants" should be --determinants --.

Column 2, line 31, "NH" should be --$NH_2$--.

Column 3, line 40. "am" should be --amino --.

Column 4, line 18, "Protein" should be --protein --.

Signed and Sealed this

Sixth Day of September, 1994

*Attest:*

BRUCE LEHMAN

*Attesting Officer*   *Commissioner of Patents and Trademarks*